(12) United States Patent
Huang et al.

(10) Patent No.: US 10,217,949 B2
(45) Date of Patent: Feb. 26, 2019

(54) ORGANIC ELECTROLUMINESCENT MATERIALS CONTAINING CARBOLINE GROUP AND ORGANIC ELECTROLUMINESCENT DEVICE BY USING THE SAME

(71) Applicant: Yuan Ze University, Chung-Li (TW)

(72) Inventors: Chiung-Hui Huang, Chung-Li (TW); Cheng-Pin Chen, Chung-Li (TW); Man-Kit Leung, Chung-Li (TW); Tien-Lung Chiu, Chung-Li (TW); Jiun-Haw Lee, Chung-Li (TW); Jau-Jiun Huang, Chung-Li (TW)

(73) Assignee: YUAN ZE UNIVERSITY, Chung-Li (TW)

( * ) Notice: Subject to any disclaimer, the term of this patent is extended or adjusted under 35 U.S.C. 154(b) by 72 days.

(21) Appl. No.: 15/411,685

(22) Filed: Jan. 20, 2017

(65) Prior Publication Data
US 2018/0040836 A1 Feb. 8, 2018

(30) Foreign Application Priority Data
Aug. 3, 2016 (TW) .............................. 105124683 A

(51) Int. Cl.
*H01L 51/50* (2006.01)
*H01L 51/00* (2006.01)
(Continued)

(52) U.S. Cl.
CPC ........ *H01L 51/0094* (2013.01); *C07F 7/0812* (2013.01); *C07F 7/0814* (2013.01);
(Continued)

(58) Field of Classification Search
None
See application file for complete search history.

(56) References Cited

U.S. PATENT DOCUMENTS

| | | | | |
|---|---|---|---|---|
| 2005/0142379 A1* | 6/2005 | Juni | ..................... | G02B 5/0242 428/690 |
| 2006/0222886 A1* | 10/2006 | Kwong | .................. | C09K 11/06 428/690 |
| 2007/0224448 A1* | 9/2007 | Ikeda | ..................... | C09K 11/06 428/690 |

FOREIGN PATENT DOCUMENTS

| | | | | |
|---|---|---|---|---|
| JP | 2009-224762 | * | 10/2009 | ............ H01L 51/50 |
| JP | 2009224762 A | | 10/2009 | |

(Continued)

*Primary Examiner* — Gregory D Clark
(74) *Attorney, Agent, or Firm* — Muncy, Geissler, Olds & Lowe, P.C.

(57) ABSTRACT

An organic electroluminescent material is shown in General Formula (1),

General Formula (1)

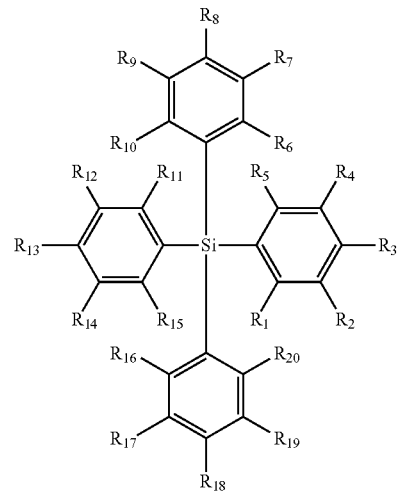

wherein $R_3$ is a carboline group, $R_{13}$ is a carbazole group or a carboline group, $R_1$ to $R_2$, $R_4$ to $R_{12}$ and $R_{14}$ to $R_{20}$ are each independently selected from the group consisting of a hydrogen atom, a fluorine atom, a cyano group, an alkyl group, a cycloalkyl group, an alkoxy (Continued)

group, a haloalkyl group, a thioalkyl group, a silyl group and an alkenyl group.

10 Claims, 1 Drawing Sheet

(51) Int. Cl.
*C07F 7/08* (2006.01)
*C09K 11/02* (2006.01)
*C09K 11/06* (2006.01)
(52) U.S. Cl.
CPC .............. *C09K 11/02* (2013.01); *C09K 11/06* (2013.01); *H01L 51/0072* (2013.01); *C09K 2211/1007* (2013.01); *C09K 2211/1014* (2013.01); *C09K 2211/1029* (2013.01); *H01L 51/0085* (2013.01); *H01L 51/5016* (2013.01)

(56) References Cited

FOREIGN PATENT DOCUMENTS

| JP | 2013-093432 | * | 5/2013 | ............. H01L 51/50 |
| KR | 20160069021 A | | 6/2016 | |

* cited by examiner

ORGANIC ELECTROLUMINESCENT MATERIALS CONTAINING CARBOLINE GROUP AND ORGANIC ELECTROLUMINESCENT DEVICE BY USING THE SAME

CROSS REFERENCE TO RELATED APPLICATIONS

This Non-provisional application claims priority under 35 U.S.C. § 119(a) on Patent Application No(s). 105124683 filed in Taiwan, Republic of China on Aug. 3, 2016, the entire contents of which are hereby incorporated by reference.

BACKGROUND OF THE INVENTION

Field of Invention

The present invention relates to an organic electroluminescent material and an organic electroluminescent device by using the same and, in particular, to an organic electroluminescent material containing at least one carboline group and an organic electroluminescent device by using the same.

Related Art

With the advances in electronic technology, a light weight and high efficiency flat display device has been developed. An organic electroluminescent device possibly becomes the mainstream of the next generation flat panel display device due to its advantages of self-luminosity, no restriction on viewing angle, power conservation, simple manufacturing process, low cost, high response speed, full color and so on.

In general, the organic electroluminescent device includes an anode, an organic luminescent layer and a cathode. When applying a direct current to the organic electroluminescent device, electron holes and electrons are injected into the organic luminescent layer from the anode and the cathode, respectively. Charge carriers move and then recombine in the organic luminescent layer because of the potential difference caused by an applied electric field. The excitons generated by the recombination of the electrons and the electron holes may excite the luminescent molecules in the organic luminescent layer. The excited luminescent molecules then release the energy in the form of light.

Nowadays, the organic electroluminescent device usually adopts a host-guest emitter system. The organic luminescent layer disposed therein includes a host material and a guest material. The electron holes and the electrons are mainly transmitted to the host material to perform recombination and thereby generate energy, and then the energy is transferred to the guest material to generate light. The guest material can be categorized into fluorescent material and phosphorescent material. Theoretically, the internal quantum efficiency can approach 100% by using appropriate phosphorescent materials. Therefore, the phosphorescent materials recently have become one of the most important developments in the field of organic electroluminescent materials.

In the development of blue host materials, the triplet energy level of the host materials must be higher than or equal to that of the guest materials to avoid the energy lost caused by reverse energy transfer. The energy lost can result in low luminous efficiency (i.e., low current efficiency) and short lifespan, etc. Therefore, it is necessary for the host materials to have greater triplet energy level. In order to increase the triple energy level of the blue host materials, much research has been focused on the single benzene ring with various ortho-substituted groups. In ortho-substitution with electron-transporting group (e.g., Oxadiazole or 3-(Biphenyl-4-yl)-5-(4-tert-butylphenyl)-4-phenyl-4H-1,2,4-triazole) and hole-transporting group (e.g., Carbazoles), a bipolar molecule is created by interrupted π-conjugated molecules due to steric hindrance.

Besides, the selection of organic electroluminescent material is not only based on the matching energy level but also the high temperature of decomposition to avoid pyrolysis caused by high temperature and also avoid the resulted decreasing of stability.

Accordingly, the present invention is provided an organic electroluminescent material containing at least one carboline group and an organic electroluminescent device by using the same which has high triplet energy level and fine thermal stability.

SUMMARY OF THE INVENTION

In view of the foregoing objectives, the invention provides a series of organic electroluminescent materials containing at least one carboline group and an organic electroluminescent device by using the same. The organic electroluminescent materials have high triplet energy level and fine thermal stability.

An organic electroluminescent material according to the present invention has a structure of the following General Formula (1).

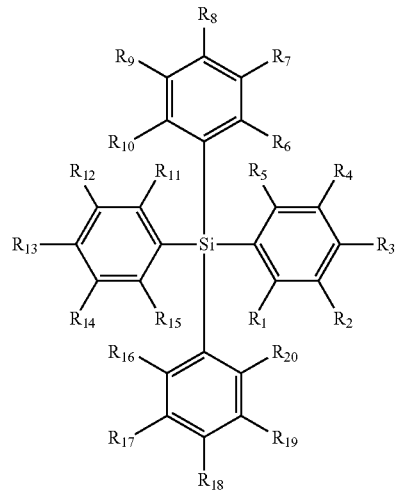

General Formula (1)

$R_3$ is a carboline group, $R_{13}$ is a carbazole group or a carboline group, $R_1$ to $R_2$, $R_4$ to $R_{12}$ and $R_{14}$ to $R_{20}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the carboline group is α-carboline group, β-carboline group or γ-carboline group.

In one embodiment, the alkyl group is selected from the group consisting of a substituted or unsubstituted straight-chain alkyl group and a substituted or unsubstituted branched-chain alkyl group. The cycloalkyl group is a substituted or unsubstituted cycloalkyl group. The alkoxy group is selected from the group consisting of a substituted or unsubstituted straight-chain alkoxy group and a substituted or unsubstituted branched-chain alkoxy group. The haloalkyl group is selected from the group consisting of a substituted or unsubstituted straight-chain haloalkyl group and a substituted or unsubstituted branched-chain haloalkyl group. The thioalkyl group is selected from the group consisting of a substituted or unsubstituted straight-chain thioalkyl group and a substituted or unsubstituted branched-chain thioalkyl group. The silyl group is selected from the group consisting of a substituted or unsubstituted straight-chain silyl group and a substituted or unsubstituted branched-chain silyl group. The alkenyl group is selected from the group consisting of a substituted or unsubstituted straight-chain alkenyl group and a substituted or unsubstituted branched-chain alkenyl group.

An organic electroluminescent device which is also provided includes a first electrode layer, a second electrode layer and an organic luminescent unit. The organic luminescent unit is disposed between the first electrode layer and the second electrode layer. The organic luminescent unit has at least an organic luminescent material as shown in General Formula (1).

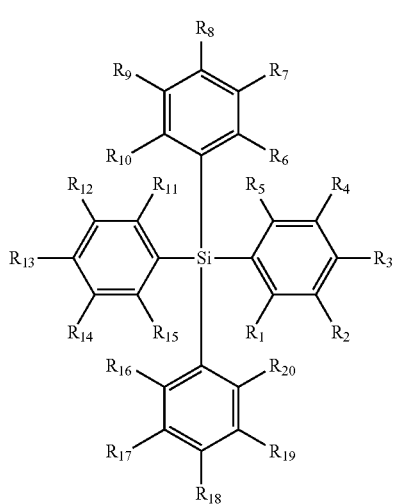

Formula (1)

$R_3$ is a carboline group, $R_{13}$ is a carbazole group or a carboline group, $R_1$ to $R_2$, $R_4$ to $R_{12}$ and $R_{14}$ to $R_{20}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

In one embodiment, the carboline group is α-carboline group, β-carboline group or γ-carboline group.

In one embodiment, the alkyl group is selected from the group consisting of a substituted or unsubstituted straight-chain alkyl group and a substituted or unsubstituted branched-chain alkyl group. The cycloalkyl group is a substituted or unsubstituted cycloalkyl group. The alkoxy group is selected from the group consisting of a substituted or unsubstituted straight-chain alkoxy group and a substituted or unsubstituted branched-chain alkoxy group. The haloalkyl group is selected from the group consisting of a substituted or unsubstituted straight-chain haloalkyl group and a substituted or unsubstituted branched-chain haloalkyl group. The thioalkyl group is selected from the group consisting of a substituted or unsubstituted straight-chain thioalkyl group and a substituted or unsubstituted branched-chain thioalkyl group. The silyl group is selected from the group consisting of a substituted or unsubstituted straight-chain silyl group and a substituted or unsubstituted branched-chain silyl group. The alkenyl group is selected from the group consisting of a substituted or unsubstituted straight-chain alkenyl group and a substituted or unsubstituted branched-chain alkenyl group.

In one embodiment, the organic luminescent unit comprises an organic luminescent layer.

In one embodiment, the organic luminescent unit further comprises a hole transport layer and an electron transport layer, wherein the organic luminescent layer is disposed between the hole transport layer and the electron transport layer.

In one embodiment, the organic luminescent unit further comprises a hole transport layer, an electron blocking layer, an electron transport layer and an electron injection layer, wherein the electron blocking layer, the organic luminescent layer and the electron transport layer are sequentially disposed between the hole transport layer and the electron injection layer.

In one embodiment, the organic luminescent layer comprises a host material and a guest material, wherein the host material is the organic electroluminescent material and the guest material is a phosphorescent material.

In one embodiment, the content of the host material in the organic luminescent layer is between 60 vol % to 95 vol %.

In one embodiment, the content of the guest material in the organic luminescent layer is between 5 vol % to 40 vol %.

As mentioned above, in the organic electroluminescent material and the organic electroluminescent device according to the present invention, a series of bipolar compounds are synthesized by utilizing a silicon atom as a spacer to link a hole-transporting carbazole group (hereinafter referred to as Cz) and an electron-transporting/hole-transporting carboline group (hereinafter referred to as Cb). Alternatively, another series of bipolar compounds are synthesized by utilizing a silicon atom as a spacer to link two electron-transporting/hole-transporting carboline groups. The bipolar compounds of the present invention having high triplet energy level and good thermal stability can be organic electroluminescent materials with high luminous efficiency.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
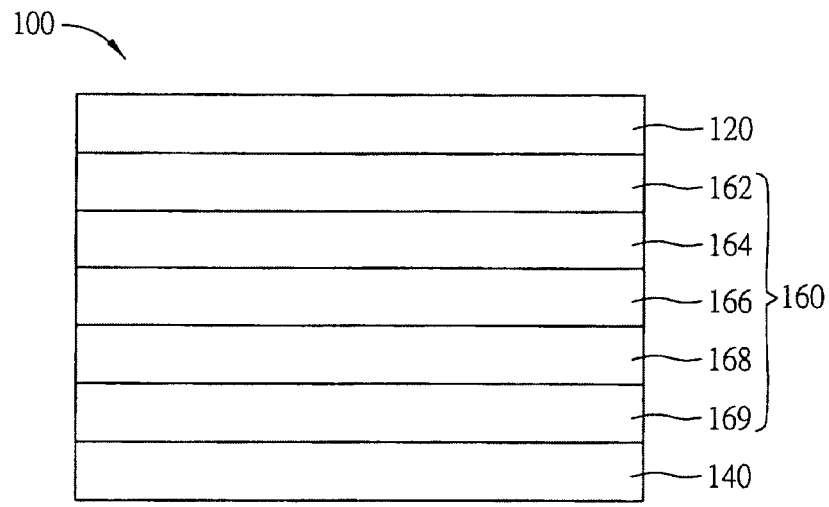
FIG. 1 is a cross-sectional schematic diagram of an organic electroluminescent device of the second embodiment according to the invention.

The embodiments of the invention will be apparent from the following detailed description, which proceeds with reference to the accompanying drawings, wherein the same references relate to the same elements.

Organic Electroluminescent Material

An organic electroluminescent material according to the first embodiment of the present invention has a structure of the following General Formula (1).

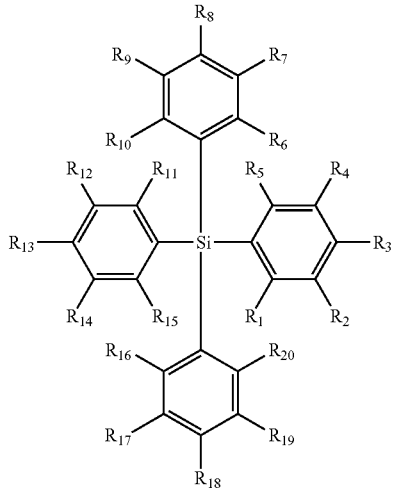

General Formula (1)

$R_3$ is a carboline group, $R_{13}$ is a carbazole group or a carboline group, $R_1$ to $R_2$, $R_4$ to $R_{12}$ and $R_{14}$ to $R_{20}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

Herein, the carboline group can be α-carboline group, β-carboline group or γ-carboline group.

In addition, the alkyl group can be selected from the group consisting of a substituted or unsubstituted straight-chain alkyl group and a substituted or unsubstituted branched-chain alkyl group. The cycloalkyl group can be a substituted or unsubstituted cycloalkyl group. The alkoxy group can be selected from the group consisting of a substituted or unsubstituted straight-chain alkoxy group and a substituted or unsubstituted branched-chain alkoxy group. The haloalkyl group can be selected from the group consisting of a substituted or unsubstituted straight-chain haloalkyl group and a substituted or unsubstituted branched-chain haloalkyl group. The thioalkyl group can be selected from the group consisting of a substituted or unsubstituted straight-chain thioalkyl group and a substituted or unsubstituted branched-chain thioalkyl group. The silyl group can be selected from the group consisting of a substituted or unsubstituted straight-chain silyl group and a substituted or unsubstituted branched-chain silyl group. The alkenyl group can be selected from the group consisting of a substituted or unsubstituted straight-chain alkenyl group and a substituted or unsubstituted branched-chain alkenyl group.

In the embodiment, the alkyl group can be preferably selected from the group consisting of a substituted or unsubstituted straight-chain alkyl group with the carbon number of 1 to 6, and a substituted or unsubstituted branched-chain alkyl group with the carbon number of 3 to 6. The cycloalkyl group can be preferably a substituted or unsubstituted cycloalkyl group with the carbon number of 3 to 6. The alkoxy group can be preferably selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group can be preferably selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group can be preferably selected from the group consisting of a substituted or unsubstituted straight-chain thioalkyl group with the carbon number of 1 to 6, and a substituted or unsubstituted branched-chain thioalkyl group with the carbon number of 3 to 6. The silyl group can be preferably selected from the group consisting of a substituted or unsubstituted straight-chain silyl group with the carbon number of 1 to 6, and a substituted or unsubstituted branched-chain silyl group with the carbon number of 3 to 6. The alkenyl group can be preferably selected from the group consisting of a substituted or unsubstituted straight-chain alkenyl group with the carbon number of 2 to 6, and a substituted or unsubstituted branched-chain alkenyl group with the carbon number of 3 to 6.

The organic electroluminescent material of General Formula (1) according to the embodiment can be a host material of an organic luminescent layer in an organic electroluminescent device. A preferred example is the compound of Chemical Formula (1), α-CbSiCz, where $R_3$ is a α-carboline group, $R_{13}$ is a carbazole group, and $R_1$ to $R_2$, $R_4$ to $R_{12}$ and $R_{14}$ to $R_{20}$ are all independent hydrogen atoms.

Chemical Formula (1)

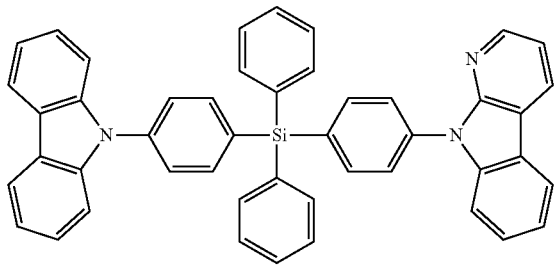

Alternatively, another preferred example is the compound of Chemical Formula (2), β-CbSiCz, where $R_3$ is a β-carboline group, $R_{13}$ is a carbazole group, and $R_1$ to $R_2$, $R_4$ to $R_{12}$ and $R_{14}$ to $R_{20}$ are all independent hydrogen atoms.

Chemical Formula (2)

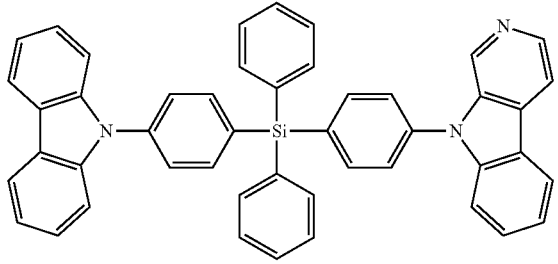

Alternatively, another preferred example is the compound of Chemical Formula (3), γ-CbSiCz, where $R_3$ is a γ-carboline group, $R_{13}$ is a carbazole group, and $R_1$ to $R_2$, $R_4$ to $R_{12}$ and $R_{14}$ to $R_{20}$ are all independent hydrogen atoms.

Chemical Formula (3)

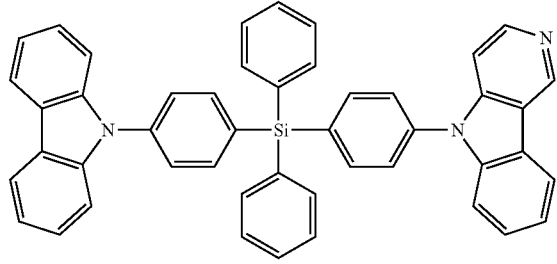

Alternatively, another preferred example is the compound of Chemical Formula (4), Di-α-CbSi, where $R_3$ and $R_{13}$ are α-carboline groups, and $R_1$ to $R_2$, $R_4$ to $R_{12}$ and $R_{14}$ to $R_{20}$ are all independent hydrogen atoms.

Chemical Formula (4)

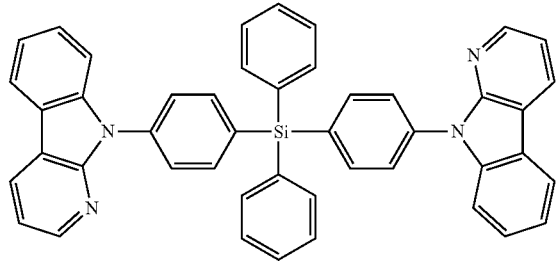

Alternatively, another preferred example is the compound of Chemical Formula (5), Di-β-CbSi, where $R_3$ and $R_{13}$ are β-carboline groups, and $R_1$ to $R_2$, $R_4$ to $R_{12}$ and $R_{14}$ to $R_{20}$ are all independent hydrogen atoms.

Chemical Formula (5)

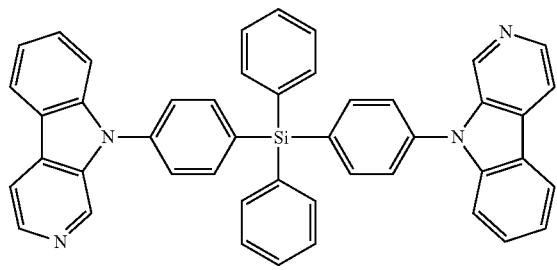

Alternatively, another preferred example is the compound of Chemical Formula (6), Di-γ-CbSi, where $R_3$ and $R_{13}$ are γ-carboline groups, and $R_1$ to $R_2$, $R_4$ to $R_{12}$ and $R_{14}$ to $R_{20}$ are all independent hydrogen atoms.

Chemical Formula (6)

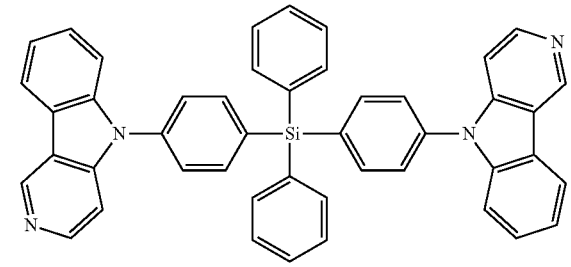

Of course, another preferred example can also be the compound, where $R_3$ is a α-carboline group and $R_{13}$ is a β-carboline group, or where $R_3$ is a β-carboline group and $R_{13}$ is a γ-carboline group. Further, another preferred example can also be the compound, where $R_3$ is a α-carboline group and $R_{13}$ is a γ-carboline group. The above description is given by way of example only and shall in no way restrict the scope of the embodiment.

In the embodiment, a series of bipolar compounds are synthesized by utilizing a silicon atom as a spacer to link a hole-transporting carbazole group and an electron-transporting/hole-transporting carboline group. Alternatively, another series of bipolar compounds are synthesized by utilizing a silicon atom to link two electron-transporting/hole-transporting carboline groups.

Herein, the bipolar compounds have high triplet energy level and good thermal stability, and can be bipolar host materials of the phosphorescent organic light-emitting diode with high luminous efficiency. In other words, the host materials according to the above-mentioned embodiment comprise an electron-transporting group and a hole-transporting group in the same molecule so as to have a characteristic of bipolar carrier-transporting.

In addition, comparing with other substituted positions, for example, ortho- or meta-position, the substituent, such as carboline group or carbazole group, attached to the benzene ring at the para-position with respect to the position of attachment to the silicon atom can have a higher yield. Moreover, when three or all of four benzene rings linked to the silicon atom have steric bulkier substituents, the substituents at the para-position can have less steric hindrance and hence have higher yield. The structure of tetraphenylsilane interrupts the conjugation system of the whole molecular so that the triple energy level of the compound can meet the requirements of the organic electroluminescent material. The substituent attached to the benzene ring at the para-position can also make molecular arrangement more uniform and have advantages of good film forming ability.

In the embodiment, the guest materials for use with the host materials may be any suitable materials applied to the organic luminescent layer of the organic electroluminescent device, for example but not limited to, Ir(2-phq)$_3$, Ir(ppy)$_3$, and FIrpic, and their structures are respectively shown as the following Chemical Formula (7), Chemical Formula (8) and Chemical Formula (9).

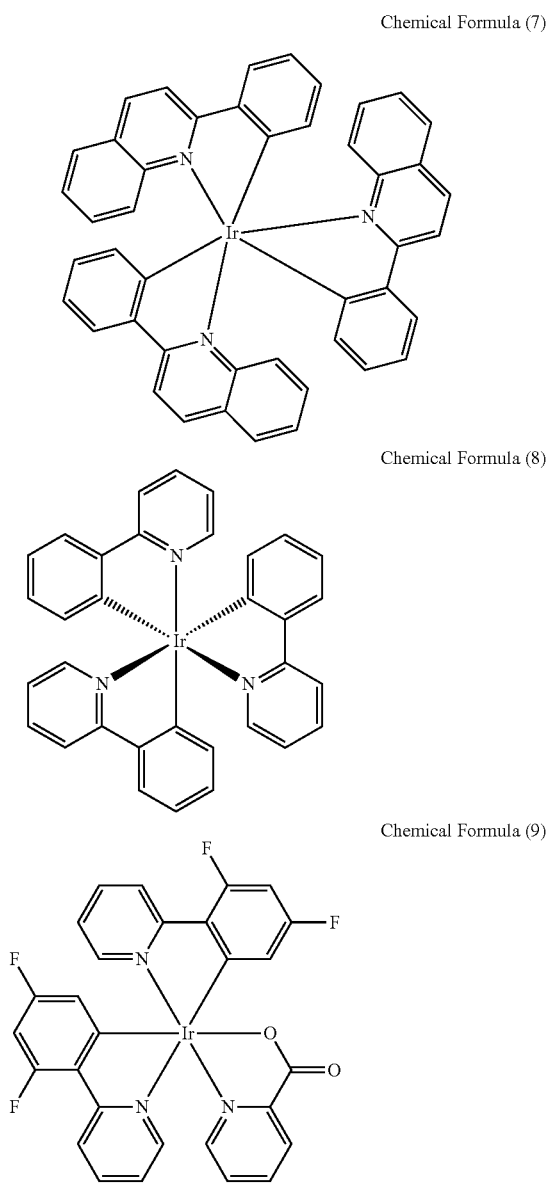

Chemical Formula (7)

Chemical Formula (8)

Chemical Formula (9)

Moreover, the materials having the structures of General Formula (1), in addition to being applied to the organic luminescent layer, can also be applied to any layer of an organic electroluminescent unit, for example, a hole injection layer, hole transport layer, electron blocking layer, electron transport layer or electron injection layer and so on.

Organic Electroluminescent Device

Please refer to FIG. 1, an organic electroluminescent device 100 of the second embodiment according to the invention includes a first electrode layer 120, a second electrode layer 140 and an organic luminescent unit 160. In the embodiment, the first electrode layer 120 can be a transparent electrode material, such as indium tin oxide (ITO), and the second electrode layer 140 can be a metal, transparent conductive substance or any other suitable conductive material. On the other hand, the first electrode layer 120 can also be a metal, transparent conductive substance or any other suitable conductive material, and the second electrode layer 140 can also be a transparent electrode material. Overall, at least one of the first electrode layer 120 and the second electrode layer 140 of the embodiment is a transparent electrode material, so that the light emitted from the organic luminescent unit 160 may pass through the transparent electrode, thereby enabling the organic electroluminescent device 100 to emit light.

In addition, please also refer to FIG. 1, the organic luminescent unit 160 can comprise a hole transport layer 162, an electron blocking layer 164, an organic luminescent layer 166, an electron transport layer 168 and an electron injection layer 169. The electron blocking layer 164, the organic luminescent layer 166 and the electron transport layer 168 are sequentially disposed between the hole transport layer 162 and the electron injection layer 169.

Herein, the materials of the hole transport layer 162 may be 1,1-Bis[4-[N,N'-di(p-tolyl)amino]phenyl]cyclohexane (TAPC), N,N-bis-(1-naphthyl)-N,N-diphenyl-1,1-biphenyl-4,4-diamine (NPB) or N—N'-diphenyl-N—N'bis(3-methylphenyl)-[1-1'-biphenyl]-4-4'-diamine (TPD) and so on. Moreover, the thickness of the hole transport layer 162 of the embodiment is, for example, less than 100 nm. In the embodiment, the hole transport layer 162 can increase the injection rate of electron holes from the first electrode layer 120 to the organic luminescent layer 166 and can also reduce the driving voltage of the organic electroluminescent device 100.

The materials of the electron blocking layer 164 may be N,N'-dicarbazolyl-3,5-benzene (mCP) or any other material with low electron affinity. In the embodiment, the thickness of the electron blocking layer 164 is, for example, less than 30 nm. The electron blocking layer 164 may further increase the transport rate of the electron hole from the hole transport layer 162 to the organic luminescent layer 166.

In addition, the thickness of the organic luminescent layer 166 of the embodiment is between 5 nm and 60 nm, the organic luminescent layer 166 includes the host material and the guest material, and the host material can be the above-mentioned organic electroluminescent material which has a structure of General Formula (1).

General Formula (1)

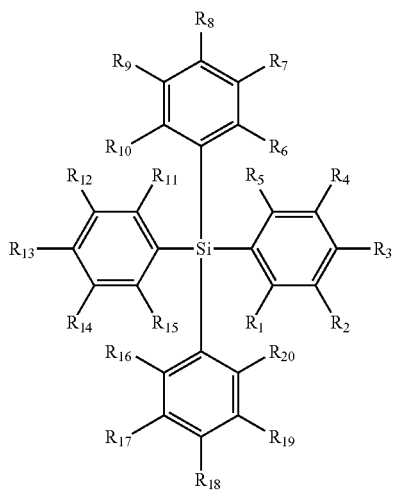

$R_3$ is a carboline group, $R_{13}$ is a carbazole group or a carboline group, $R_1$ to $R_2$, $R_4$ to $R_{12}$ and $R_{14}$ to $R_{20}$ are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group.

Herein, the carboline group can be α-carboline group, β-carboline group or γ-carboline group.

In addition, the alkyl group can be selected from the group consisting of a substituted or unsubstituted straight-chain alkyl group with the carbon number of 1 to 6, and a substituted or unsubstituted branched-chain alkyl group with the carbon number of 3 to 6. The cycloalkyl group can be a substituted or unsubstituted cycloalkyl group with the carbon number of 3 to 6. The alkoxy group can be selected from the group consisting of a substituted or unsubstituted straight-chain alkoxy group with the carbon number of 1 to 6, and a substituted or unsubstituted branched-chain alkoxy group with the carbon number of 3 to 6. The haloalkyl group can be selected from the group consisting of a substituted or unsubstituted straight-chain haloalkyl group with the carbon number of 1 to 6, and a substituted or unsubstituted branched-chain haloalkyl group with the carbon number of 3 to 6. The thioalkyl group can be selected from the group consisting of a substituted or unsubstituted straight-chain thioalkyl group with the carbon number of 1 to 6, and a substituted or unsubstituted branched-chain thioalkyl group with the carbon number of 3 to 6. The silyl group can be preferably selected from the group consisting of a substituted or unsubstituted straight-chain silyl group with the carbon number of 1 to 6, and a substituted or unsubstituted branched-chain silyl group with the carbon number of 3 to 6. The alkenyl group can be preferably selected from the group consisting of a substituted or unsubstituted straight-chain alkenyl group with the carbon number of 2 to 6, and a substituted or unsubstituted branched-chain alkenyl group with the carbon number of 3 to 6.

A preferred example is the compound of Chemical Formula (1), α-CbSiCz, where $R_3$ is a α-carboline group, $R_{13}$ is a carbazole group, and $R_1$ to $R_2$, $R_4$ to $R_{12}$ and $R_{14}$ to $R_{20}$ are all independent hydrogen atoms.

Chemical Formula (1)

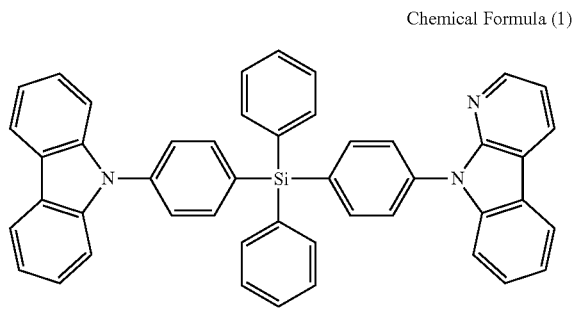 [SMILES: c1ccc([Si](c2ccccc2)(c2ccc(-n3c4ccccc4c4ccccc43)cc2)c2ccc(-n3c4ccccc4c4cccnc43)cc2)cc1]

Alternatively, another preferred example is the compound of Chemical Formula (2), β-CbSiCz, where $R_3$ is a β-carboline group, $R_{13}$ is a carbazole group, and $R_1$ to $R_2$, $R_4$ to $R_{12}$ and $R_{14}$ to $R_{20}$ are all independent hydrogen atoms.

Chemical Formula (2)

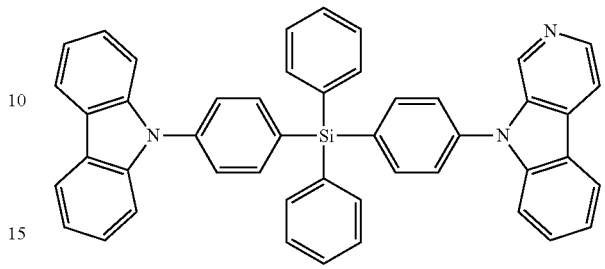

Alternatively, another preferred example is the compound of Chemical Formula (3), γ-CbSiCz, where $R_3$ is a γ-carboline group, $R_{13}$ is a carbazole group, and $R_1$ to $R_2$, $R_4$ to $R_{12}$ and $R_{14}$ to $R_{20}$ are all independent hydrogen atoms.

Chemical Formula (3)

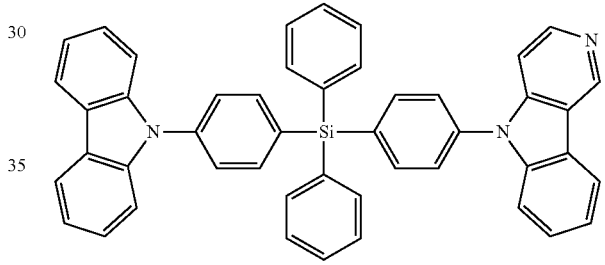

Alternatively, another preferred example is the compound of Chemical Formula (4), Di-α-CbSi, where $R_3$ and $R_{13}$ are α-carboline groups, and $R_1$ to $R_2$, $R_4$ to $R_{12}$ and $R_{14}$ to $R_{20}$ are all independent hydrogen atoms.

Chemical Formula (4)

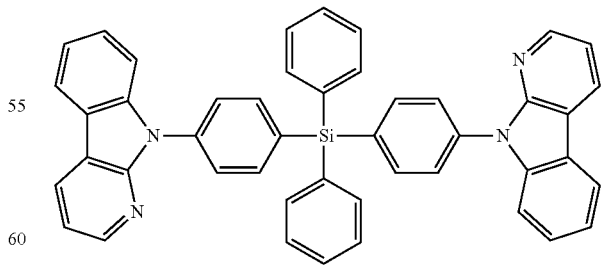

Alternatively, another preferred example is the compound of Chemical Formula (5), Di-β-CbSi, where $R_3$ and $R_{13}$ are β-carboline groups, and $R_1$ to $R_2$, $R_4$ to $R_{12}$ and $R_{14}$ to $R_{20}$ are all independent hydrogen atoms.

Chemical Formula (5)

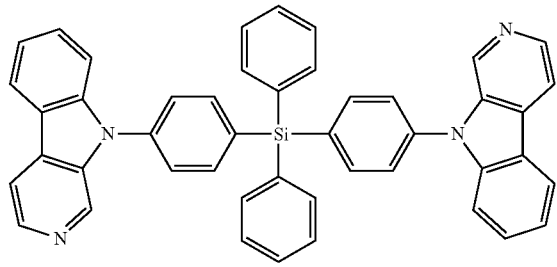

Alternatively, another preferred example is the compound of Chemical Formula (6), Di-γ-CbSi, where $R_3$ and $R_{13}$ are γ-carboline groups, and $R_1$ to $R_2$, $R_4$ to $R_{12}$ and $R_{14}$ to $R_{20}$ are all independent hydrogen atoms.

Chemical Formula (6)

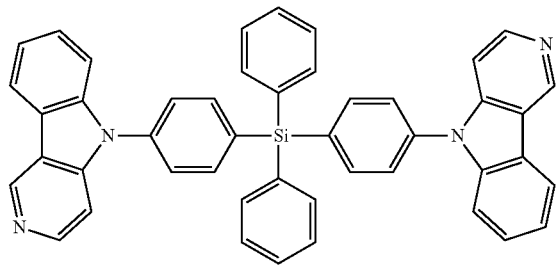

Of course, another preferred example can also be the compound, where $R_3$ is a α-carboline group and $R_{13}$ is a β-carboline group, or where $R_3$ is a β-carboline group and $R_{13}$ is a γ-carboline group. Further, another preferred example can also be the compound, where $R_3$ is a α-carboline group and $R_{13}$ is a γ-carboline group. The above description is given by way of example only and shall in no way restrict the scope of the embodiment.

In addition, the content of the host material in the organic luminescent layer 166 is between 60 vol % to 95 vol %. Moreover, the content of the guest material in the organic luminescent layer 166 is between 5 vol % to 40 vol %.

Moreover, the guest materials may be any suitable materials applied to the organic luminescent layer, for example but not limited to, $Ir(2-phq)_3$, $Ir(ppy)_3$, and FIrpic, and their structures are respectively shown as the following Chemical Formula (7), Chemical Formula (8) and Chemical Formula (9).

Chemical Formula (7)

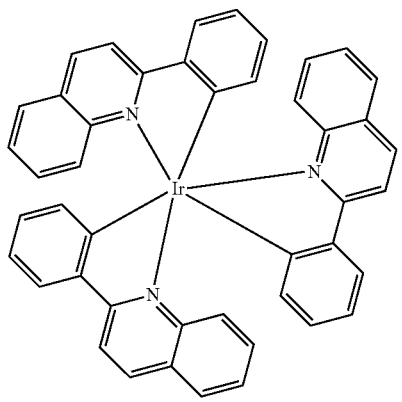

Chemical Formula (8)

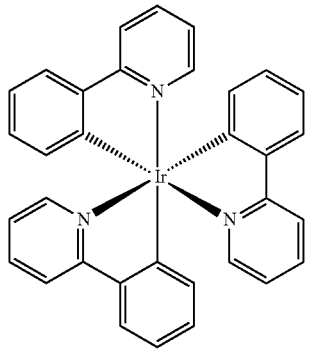

Chemical Formula (9)

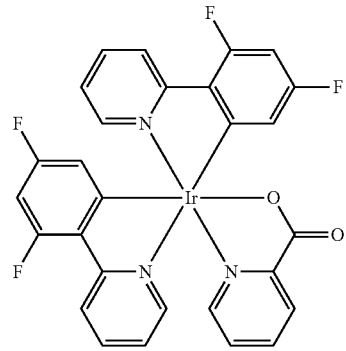

In addition, the material of the electron transport layer 168 may be, but not limited to, a metal complex, such as Tris-(8-hydroxy-quinoline)aluminum ($Alq_3$), bis(10-hydroxybenzo-[h]quinolinato)beryllium ($BeBq_2$) and so on, or a heterocyclic compound, such as 2-(4-Biphenylyl)-5-(4-tert-butylphenyl)-1,3,4-oxadiazole (PBD), 3-(4-Biphenylyl)-4-phenyl-5-tert-butylphenyl-1,2,4-triazole (TAZ), 2,2', 2"-(1,3,5-Benzinetriyl)-tris(1-phenyl-1-H-benzimidazole) (TPBI), diphenylbis(4-(pyridin-3-yl)phenyl)silane (DPPS) and so on. In the embodiment, the thickness of the electron transport layer 168 may be, for example, less than 100 nm. The electron transport layer 168 can facilitate the transfer of electrons from the second electrode layer 140 to the organic luminescent layer 166 so as to increase the transport rate of the electron. Moreover, the material of the electron injection layer 169 may be, for example, LiF. The thickness of the electron injection layer 169 may be, for example, 0.9 nm.

Figure 2:
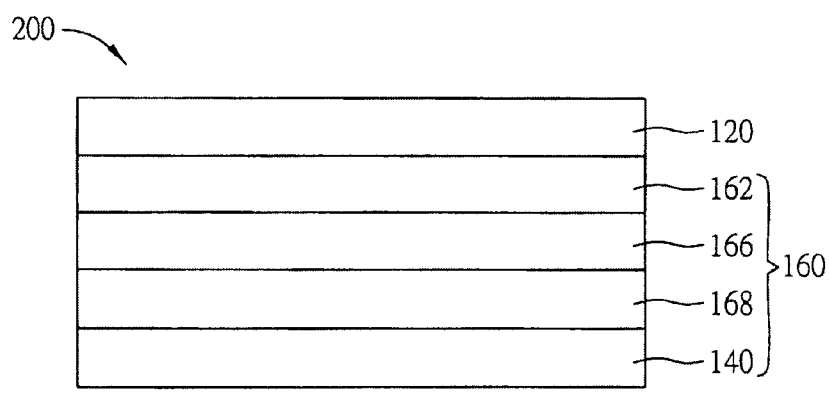
FIG. 2 is a cross-sectional schematic diagram of an organic electroluminescent device of the third embodiment according to the invention.

In addition, FIG. 2 is a cross-sectional schematic diagram of an organic electroluminescent device 200 of the third embodiment according to the invention. The configuration of the organic electroluminescent device 200 is substantially similar with that of the organic electroluminescent device 100, and same elements have substantial the same characteristics and functions. Therefore, the similar references relate to the similar elements, and detailed explanation is omitted hereinafter.

Please refer to FIG. 2, in the embodiment, the organic luminescent unit 160 can comprise a hole transport layer 162, an organic luminescent layer 166 and an electron transport layer 168. The organic luminescent layer 166 is disposed between the hole transport layer 162 and the electron transport layer 168.

Figure 3:
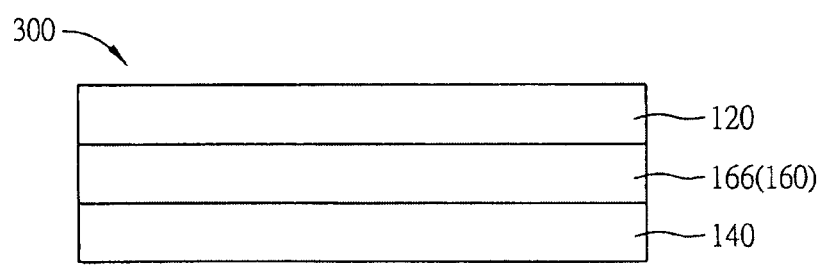
FIG. 3 is a cross-sectional schematic diagram of an organic electroluminescent device of the fourth embodiment according to the invention.

In addition, FIG. 3 is a cross-sectional schematic diagram of an organic electroluminescent device 300 of the fourth embodiment according to the invention. The configuration of the organic electroluminescent device 300 is substantially similar with that of the organic electroluminescent device 100, and same elements have substantial the same characteristics and functions. Therefore, the similar references relate to the similar elements, and detailed explanation is omitted hereinafter.

Please refer to FIG. 3, in the embodiment, the organic luminescent unit 160 can comprise an organic luminescent layer 166.

The configuration of the organic electroluminescent device according to the invention is not limited to what is disclosed in the second, third or fourth embodiment. The second, third and fourth embodiments are embodiments for illustration.

To illustrate the synthesis of Chemical Formula (1) to Chemical Formula (6) and compound 1 to compound 8, there are several examples shown below.

Example 1: Synthesis of 3-chloro-N-phenylpyridin-2-amine 2, 3-Dichloropyridine (2.96 g, 20.0 mmol), palladium (II) acetate (220.0 mg, 1.0 mmol), triphenylphosphine (520.0 mg, 2.0 mmol), sodium tert-butoxide (2.30 g, 24.0 mmol) and a stir bar were placed in a 100 mL wide mouth double-neck bottle. The deoxygenated anhydrous o-xylene (50.00 mL) and aniline (1.86 mL, 22.0 mmol) were injected by using cannula under an argon system. After the mixture were refluxed at 120□ for 24 hours, the temperature was returned to room temperature. The mixture was filtered through celite, and then the solvent was removed through distillation under reduced pressure. The residue was purified by column chromatography using a mixture of dichloromethane and n-hexane (1:5) as eluent and compound 1 as a light yellow oil (3.22 g, yield: 78.7%) was obtained. Spectral data as follow: $^1$H NMR (400 MHz, $d_6$-DMSO): δ 8.33 (s, 1H), 8.09 (d, J=4.8 Hz, 1H), 7.76 (d, J=7.6 Hz, 1H), 7.68 (d, J=8.4 Hz, 2H), 7.28 (t, J=7.6 Hz, 2H), 7.00-6.96 (m, 1H), 6.82-6.79 (m, 1H); $^{13}$C NMR (100 MHz, $d_6$-DMSO): δ 152.05, 146.27, 141.09, 138.02, 128.96, 122.68, 121.23, 116.34, 116.16. The above reaction is represented by the chemical equation (1).

Chemical equation (1)

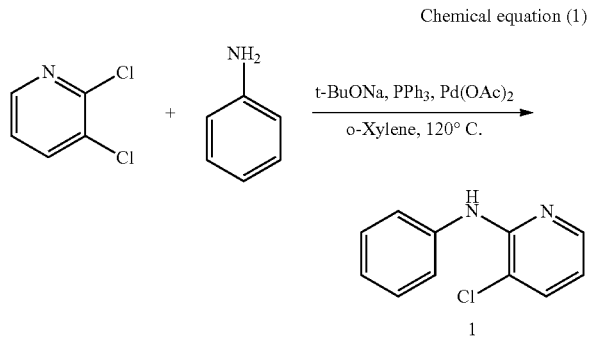

Example 2: Synthesis of 9H-pyrido[2,3-b]indole

Compound 1 (3.22 g, 15.7 mmol), palladium (II) acetate (220.0 mg, 1.0 mmol) and tricyclohexylphosphine tetrafluoroborate (740.0 mg, 2.0 mmol) were placed in a double neck bottle. The deoxygenated anhydrous dimethylacetaminde (50.00 mL) and 1,8-diazabicycloundec-7-ene (0.71 mL, 4.0 mmol) were injected by using cannula under an argon system. After the mixture was refluxed at 165° C. for 24 hours, the temperature was returned to room temperature. The mixture was filtered through celite and washed with ethyl acetate. Then, the solvent was removed through distillation under reduced pressure. The residue was purified by column chromatography using a mixture of n-hexane and ethyl acetate (1:1) as eluent and compound 2 as a yellow solid (9H-pyrido[2,3-b]indole, i.e. α-carboline, 1.265 g, yield: 48%) was obtained. Spectral data as follow: $^1$H NMR (400 MHz, $d_6$-DMSO): δ 11.82 (s, 1H), 8.48 (dd, J=1.2, 1.6 Hz, 1H), 8.42 (dd, J=0.8, 3.2 Hz, 1H), 8.41-8.13 (m, 1H), 7.54-7.52 (m, 1H), 7.47-7.43 (m, 1H), 7.23-7.17 (m, 1H); $^{13}$C NMR (100 MHz, $d_6$-DMSO): δ 151.40, 145.52, 138.29, 127.80, 126.04, 120.59, 119.86, 118.85, 114.65, 114.40, 110.71. The above reaction is represented by the chemical equation (2).

Chemical equation (2)

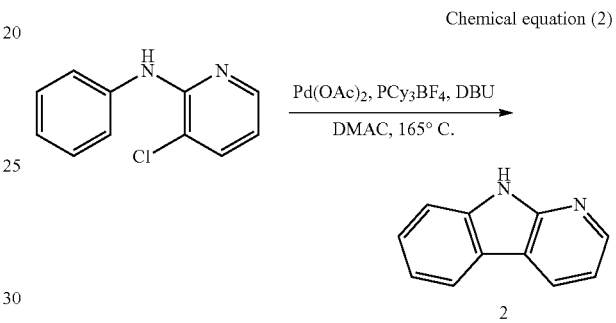

Example 3: Synthesis of 2,3,4,9-tetrahydro-1H-pyrido[3,4-b]indole

Glyoxylic acid monohydrate (12.66 g, 137.6 mmol) was dissolved in 30.0 mL of deionized water. In addition, tryptamine (20.0 g, 124.5 mmol) was mixed with 380.0 mL of deionized water and treated with 3 drops of HCl to assist tryptamine to dissolve in deionized water. The aqueous solution of tryptamine is orange-yellow cloudy at this time. Before tryptamine was completely dissolved in deionized water, the two above aqueous solutions were mixed and stirred about 15 minutes at room temperature. Then, white emulsion is precipitated in the mixed aqueous solution. In addition, KOH (6.8 g) was dissolved in 34.0 mL of deionized water. The aqueous solution of KOH were slowly added in the mixed aqueous solution and then HCl was added until a PH of about 4. The mixture was stirred for one hour at room temperature, and then placed in a refrigerator for 12 hours. After taking out from the refrigerator, a solid was collected by suction filtration. Then, 320.00 mL of deionized water and 60.00 mL of HCl were added and refluxed for 30 minutes. Again, 60.00 mL of HCl was added and refluxed for 15 minutes, then cooled to room temperature. The mixed solution was placed in the refrigerator for 2 days and the precipitate was collected. The precipitate was added in deionized water and heated to 550 so that the precipitate was dissolved and a dark green mixed aqueous solution was obtained. KOH was added in the mixed aqueous solution until a pH of about 12 and then a large amount of light green solid was precipitated. The solid compound 3 (2,3,4,9-tetrahydro-1H-pyrido[3,4-b]indole, 18.19 g, yield: 84%) was collected by suction filtration. Spectral data as follow: $^1$H NMR (400 MHz, $d_6$-DMSO): δ 10.67 (s, 1H), 7.34 (d, J=7.6 Hz, 1H), 7.26 (d, J=8.0 Hz, 1H), 6.99 (m, 1H), 6.94-6.93 (m, 1H), 3.86 (s, 2H), 3.08 (br s, 2H), 2.98 (t, J=5.2 Hz, 2H), 2.59 (m, 2H); $^{13}$C NMR (100 MHz, $d_6$-DMSO): δ 134.99, 133.68, 126.76, 119.67, 117.60, 116.64, 110.27, 106.42, 42.87, 42.14, 21.67. The above reaction is represented by the chemical equation (3).

Chemical equation (3)

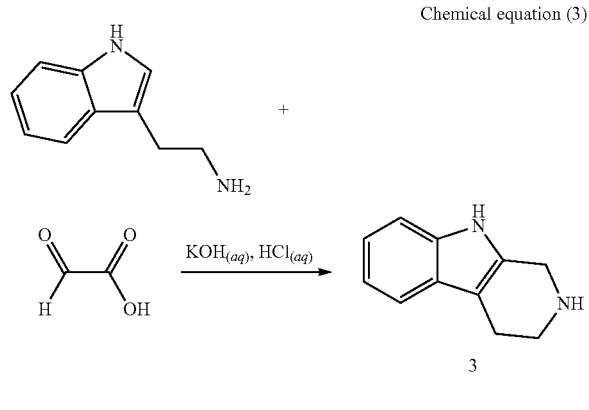

Example 4: Synthesis of 9H-pyrido[3,4-b]indole

Compound 3 (5.11 g, 29.7 mmol) and Pd/C (10%, 2.0 g) were added in 150.00 mL of p-xylene and followed by refluxed at 145° C. for 48 hours, then the temperature was returned to room temperature. The mixture was filtered through celite and then washed with methanol. The solvent was removed in a rotary evaporator to obtain compound 4 (9H-pyrido[3,4-b]indole, i.e. β-carboline, 2.48 g, yield: 49.5%) as a light yellow solid. Spectral data as follow: $^1$H NMR (400 MHz, $d_6$-DMSO): δ 11.63 (s, 1H), 8.90 (s, 1H), 8.34 (d, J=4.0 Hz, 1H), 8.24 (d, J=8.0 Hz, 1H), 8.11 (d, J=0.8 Hz, 1H), 7.61-7.54 (m, 2H), 7.24 (m, 1H); $^{13}$C NMR (100 MHz, $d_6$-DMSO): δ 140.00, 137.58, 135.46, 133.50, 127.57, 126.91, 121.26, 120.08, 114.11, 111.42. The above reaction is represented by the chemical equation (4).

Chemical equation (4)

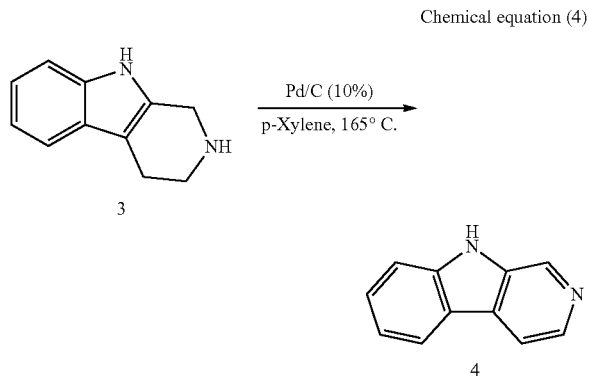

Example 5: Synthesis of N-(2-bromophenyl)pyridin-4-amine 4-aminopyridine (2.832 g, 30.0 mmol), sodium tert-butoxide (3.420 g, 35.7 mmol), 1,1'-Bis(diphenylphosphino)ferrocene (600.0 mg, 1.1 mmol) and tris(dibenzylideneacetone)-dipalladium (411.0 mg, 0.5 mmol) were placed in a 250.0 mL double neck bottle. The anhydrous toluene (90.00 mL) was injected by using cannula under an argon system. After the mixture was refluxed at 115° C. for 24 hours, the temperature was returned to room temperature. The mixture was filtered through celite, and washed with ether. The residue was purified by column chromatography using a mixture of dichloromethane and methanol (15:1) as eluent and compound 5 (N-(2-bromophenyl)pyridin-4-amine, 7.50 g, yield: 95%) as a gray solid was obtained. Spectral data as follow: 1H NMR (400 MHz, $d_6$-DMSO): δ 8.47 (s, 1H), 8.17 (d, J=6.4 Hz, 2H), 7.72-7.70 (m, 1H), 7.42-7.39 (m, 2H), 7.15-7.13 (m, 1H), 6.71 (dd, J=1.2, 1.2 Hz, 2H); $^{13}$C NMR (100 MHz, $d_6$-DMSO): δ 150.10, 149.20, 137.68, 132.83, 128.00, 125.73, 125.03, 108.43. The above reaction is represented by the chemical equation (5).

Chemical equation (5)

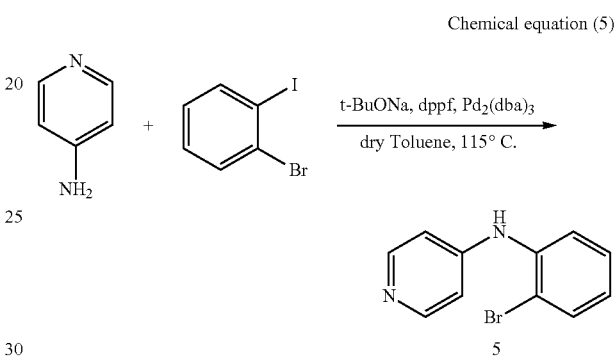

Example 6: Synthesis of 5H-pyrido[4,3-b]indole

Compound 5 (7.5 g, 30.2 mmol), palladium(II) acetate (336.0 mg, 1.5 mmol), sodium carbonate (4.44 g, 42.0 mmol) were added in 60.0 mL of dimethylformamide and followed by refluxed at 165° C. for 24 hours. Then the temperature was returned to room temperature. The mixture was filtered through celite and washed with ethyl acetate. Then, the most of ethyl acetate was removed in a rotary evaporator. NaOH was added in the solution until a neutral pH to obtain a black suspension. The filtrate was collected by suction filtration and followed by added NaOH. Then a large amount of white solid was precipitated. The solid was collected by suction filtration and followed by washed with ether to obtain compound 6 (5H-pyrido[4,3-b]indole, i.e. γ-carboline, yield: 50.89%). Spectral data as follow: $^1$H NMR (400 MHz, $d_6$-DMSO): δ 11.71 (s, 1H), 9.33 (s, 1H), 8.42 (d, J=5.6 Hz, 1H), 8.23 (d, J=8.0 Hz, 1H), 7.57-7.55 (m, 1H), 7.49-7.45 (m, 2H), 7.28-7.24 (in, 1H); $^{13}$C NMR (100 MHz, $d_6$-DMSO): δ 203.10, 144.00, 143.00, 142.24, 139.01, 126.07, 120.20, 120.09, 119.45, 118.89, 110.95, 105.84. The above reaction is represented by the chemical equation (6).

Chemical equation (6)

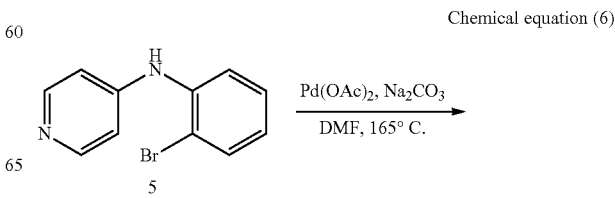

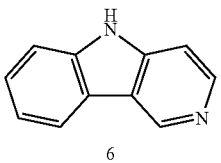

6

Example 7: Synthesis of bis(4-bromophenyl)diphenylsilane

A stir bar was placed in a 250 mL dry double neck bottle and followed by flushed and purged by nitrogen three times to be used later. A separatory funnel was installed. 1,4-dibromobenzene (11.7 mg, 50 mmol) was dissolved in anhydrous ether (100 mL) dried by sodium under an argon system and followed by cooling the temperature of the system to 0° C. To the solution was slowly added n-BuLi (1.6 M, 36 mL, 55 mmol) via the separatory funnel and react for 2 hours under the system temperature at 0° C. Ether (50 mL) and dichlorodiphenylsilane (5.27 mL, 25 mmol) were slowly added in the double neck bottle via the separatory funnel, and the solution is bright yellow at this time. Then, the solution was reacted 24 hours at room temperature to become white cloudy. After quenched with water, ether was removed in a rotary evaporator. Again, quenched with dichloromethane, and the organic layer was dried and condensed. Followed by recrystallized from dichloromethane/methylene, compound 7 (bis(4-bromophenyl)diphenylsilane, 9.08 g, yield: 73%) as a white solid was obtained. Spectral data as follow: $^1$H NMR (400 MHz, CDCl$_3$) δ7.54-7.48 (m, 8H), 7.45 (t, J=7.32 Hz, 2H), 7.41-7.35 (m, 8H); $^{13}$C NMR (100 MHz, CDCl$_3$) δ137.80, 136.20, 132.96, 132.62, 131.19, 129.99, 128.08, 124.95. The above reaction is represented by the chemical equation (7).

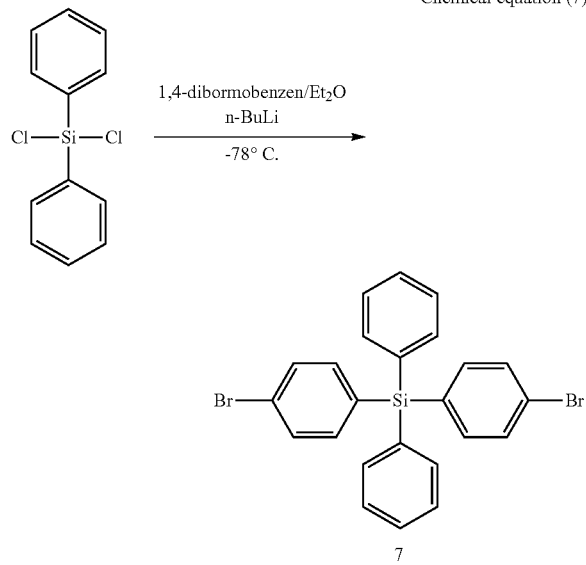

Example 8: Synthesis of 9-(4-((4-bromophenyl)diphenylsilyl)phenyl)-9H-carbazole Compound 7 (4.42 g, 9.0 mmol), carbazole (1.01 g, 6 mmol), K$_3$PO$_4$ (2.8 g, 13.2 mmol), CuI (104 mg, 0.6 mmol) and a stir bar were placed in a 50 mL single neck bottle. Toluene (30 mL) and (±)-trans-1,2-diaminocyclohexane (0.03 mL, 0.6 mmol) were injected in the single neck bottle, and a condenser was installed. After reacted at 110° C. for 24 hours, the temperature was returned to room temperature. Toluene was removed in a rotary evaporator, and the mixture was filtered through celite. The filtrate was purified by column chromatography using a mixture of dichloromethane and n-hexane (1:8) as eluent and compound 8 (9-(4-((4-bromophenyl)diphenylsilyl)phenyl)-9H-carbazole, 1.7 g, yield: 55%) as a white snowflake solid was obtained. Spectral data as follow: $^1$H NMR (400 MHz, CDCl$_3$) δ8.15 (d, J=7.7 Hz, 2H), 7.80 (dd, J=8.1, 11.1 Hz, 2H), 7.70-7.56 (m, 8H), 7.54-7.38 (m, 12H), 7.33-7.27 (m, 2H); $^{13}$C NMR (100 MHz, CDCl$_3$) δ140.48, 137.92, 137.78, 136.40, 136.32, 133.24, 132.90, 131.25, 130.01, 128.14, 128.01, 126.19, 125.94, 124.96, 123.51, 120.32, 120.10, 109.85. The above reaction is represented by the chemical equation (8).

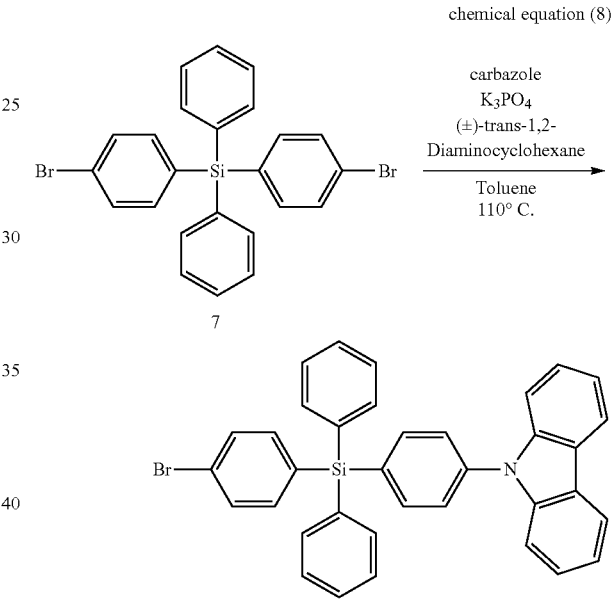

Example 9: Synthesis of Chemical Formula (1) (α-CbSiCz)

Compound 8 (1.33 g, 2.3 mmol), compound 2 (0.425 g, 2.53 mmol), K$_3$PO$_4$ (1.08 g, 5.0 mmol), CuI (43.5 mg, 0.2 mmol) and a stir bar were placed in a 50 mL single neck bottle. Toluene (12 mL) and (±)-trans-1,2-diaminocyclohexane (0.03 mL, 0.2 mmol) were injected in the single neck bottle, and a condenser was installed. After reacted at 110° C. for 24 hours, the temperature was returned to room temperature. Toluene was removed in a rotary evaporator, and the mixture was filtered through celite. The filtrate was purified by column chromatography using a mixture of dichloromethane and n-hexane (1:2) as eluent and compound of Chemical Formula (1), α-CbSiCz (9-(4-((4-(9H-carbazol-9-yl)phenyl)diphenylsilyl)phenyl)-9H-pyrido[2,3-b]indole, 0.93 g, yield: 60%) as a white solid was obtained. Spectral data as follow: $^1$H NMR (400 MHz, CD$_2$Cl$_2$) δ8.46-8.41 (m, 2H), 8.16 (d, J=7.7 Hz, 2H), 7.92 (dd, J=7.9, 5.3 Hz, 4H), 7.79-7.76 (m, 6H), 7.69 (d, J=8.1 Hz, 2H), 7.63

(d, J=8.1 Hz, 1H), 7.56-7.49 (m, 10H), 7.43 (t, J=7.7 Hz, 2H), 7.37-7.27 (m, 4H); $^{13}$C NMR (100 MHz, CD$_2$Cl$_2$) δ147.18, 146.67, 140.96, 140.08, 139.50, 138.33, 137.82, 136.82, 134.04, 133.52, 133.50, 130.37, 128.65, 128.53, 127.34, 126.97, 126.58, 126.36, 123.82, 121.41, 121.37, 121.28, 120.60, 120.45, 116.91, 116.75, 116.70, 110.82, 110.27; HRMS (EI) m/z calcd for C$_{47}$H$_{33}$N$_3$Si, 668.2524 (M+H$^+$), obsd. 668.2442. Anal. Calcd for C$_{47}$H$_{33}$N$_3$Si: C, 84.52; H, 4.98; N, 6.29. Found: C, 84.15; H, 5.04; N, 6.25. The above reaction is represented by the chemical equation (9).

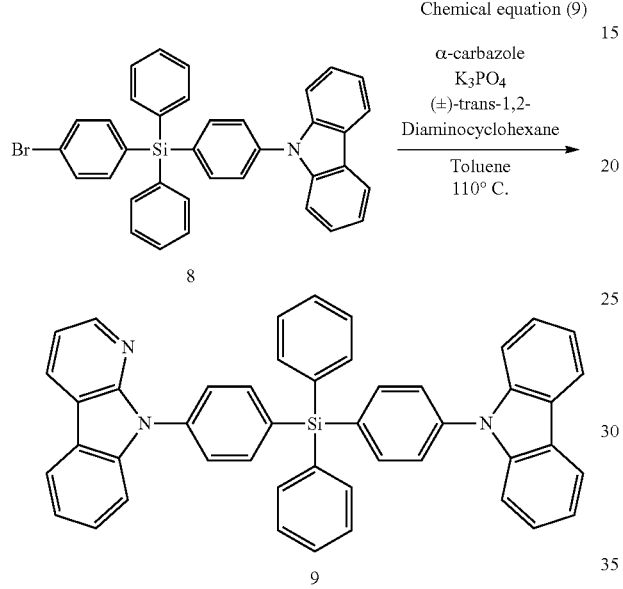

Example 10: Synthesis of Chemical Formula (2) (β-CbSiCz)

Compound 8 (1.33 g, 2.3 mmol), compound 4 (0.425 g, 2.53 mmol), K$_3$PO$_4$ (1.08 g, 5.0 mmol), CuI (43.5 mg, 0.2 mmol) and a stir bar were placed in a 50 mL single neck bottle. Toluene (12 mL) and (+)-trans-1,2-diaminocyclohexane (0.03 mL, 0.2 mmol) were injected in the single neck bottle, and a condenser was installed. After reacted at 110° C. for 24 hours, the temperature was returned to room temperature. Toluene was removed in a rotary evaporator, and the mixture was filtered through celite. The filtrate was purified by column chromatography using a mixture of ethyl acetate and dichloromethane (1:10) as eluent, and a yellow solid (1.10 g, yield: 72 g) was obtained. The yellow solid was sublimed to obtain the compound of Chemical Formula (2), 13-CbSiCz (9-(4-((4-(9H-carbazol-9-yl)phenyl)diphenylsilyl)phenyl)-9H-pyrido[3,4-b]indole). Spectral data as follow: $^1$H NMR (400 MHz, CDCl$_3$) δ8.95 (s, 1H), 8.53 (d, J=5.1 Hz, 1H), 8.19 (d, J=7.7 Hz, 1H), 8.14 (d, J=7.7 Hz, 2H), 8.01 (d, J=5.1 Hz, 1H), 7.89 (dd, J=12.8, 8.1 Hz, 4H), 7.73 (dd, J=7.5, 1.5 Hz, 4H), 7.67 (dd, J=8.1, 3.4 Hz, 4H), 7.59-7.47 (m, 10H), 7.41 (t, J=7.3 Hz, 2H), 7.35 (t, J=7.3 Hz, 1H), 7.30-7.27 (m, 2H); $^{13}$C NMR (100 MHz, CDCl$_3$) δ141.49, 140.75, 140.42, 139.52, 138.53, 138.37, 138.14, 136.91, 136.67, 134.34, 133.59, 133.54, 133.16, 130.36, 129.37, 128.88, 128.48, 126.52, 126.23, 126.22, 123.79, 122.10, 122.00, 121.07, 120.58, 120.38, 114.78, 110.93, 110.13; HRMS (EI) m/z calcd for C$_{47}$H$_{33}$N$_3$Si, 668.2524 (M+H$^+$), obsd. 668.2508. Anal. Calcd for C$_{47}$H$_{33}$N$_3$Si: C, 84.52; H, 4.98; N, 6.29. Found: C, 84.20; H, 5.08; N, 6.29. The above reaction is represented by the chemical equation (10).

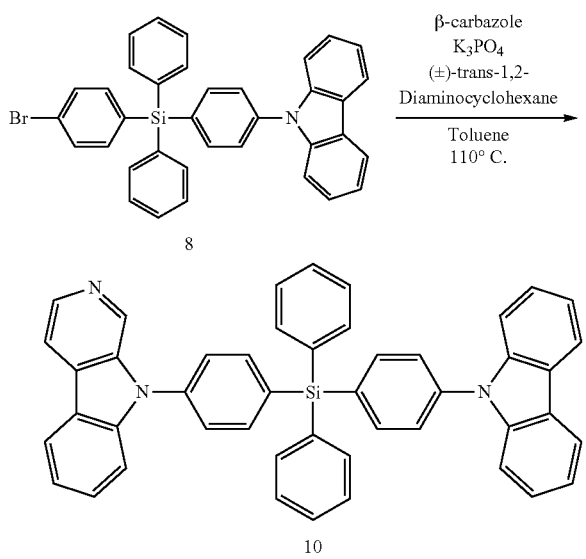

Example 11: Synthesis of Chemical Formula (3) (γ-CbSiCz)

Compound 8 (1.33 g, 2.3 mmol), compound 6 (0.425 g, 2.53 mmol), K$_3$PO$_4$ (1.08 g, 5.0 mmol), CuI (43.5 mg, 0.2 mmol) and a stir bar were placed in a 50 mL single neck bottle. Toluene (12 mL) and (±)-trans-1,2-diaminocyclohexane (0.03 mL, 0.2 mmol) were injected in the single neck bottle, and a condenser was installed. After reacted at 110° C. for 24 hours, the temperature was returned to room temperature. Toluene was removed in a rotary evaporator, and the mixture was filtered through celite. The filtrate was purified by column chromatography using a mixture of ethyl acetate and dichloromethane (1:3) as eluent. Followed by sublimed, the compound of Chemical Formula (3), γ-CbSiCz (5-(4-((4-(9H-carbazol-9-yl)phenyl)diphenylsilyl)phenyl)-5H-pyrido[4,3-b]indole, 0.81 g, yield: 53%) as a white solid was obtained. Spectral data as follow: $^1$H NMR (400 MHz, CDCl$_3$) δ9.38 (s, 1H), 8.52 (d, J=5.6 Hz, 1H), 8.21 (d, J=8.1 Hz, 1H), 8.14 (d, J=7.7 Hz, 2H), 7.89 (dd, J=15.4, 8.1 Hz, 4H), 7.72 (d, J=1.3 Hz, 4H), 7.67-7.61 (m, 4H), 7.56-7.46 (m, 10H), 7.43-7.38 (m, 4H), 7.29 (t, J=7.2 Hz, 2H); $^{13}$C NMR (100 MHz, CDCl$_3$) δ159.55, 144.95, 144.77, 142.46, 140.87, 140.66, 139.47, 138.18, 137.91, 137.88, 136.44, 134.88, 133.35, 132.96, 130.16, 128.28, 127.28, 126.38, 126.04, 125.99, 123.68, 121.91, 121.80, 120.84, 120.37, 120.21, 110.52, 109.88, 105.26; HRMS (EI) m/z calcd for C$_{47}$H$_{33}$N$_3$Si, 668.2524 (M+H$^+$), obsd. 668.2516. Anal. Calcd for C$_{47}$H$_{33}$N$_3$Si: C, 84.52; H, 4.98; N, 6.29. Found: C, 84.50; H, 4.96; N, 6.30. The above reaction is represented by the chemical equation (11).

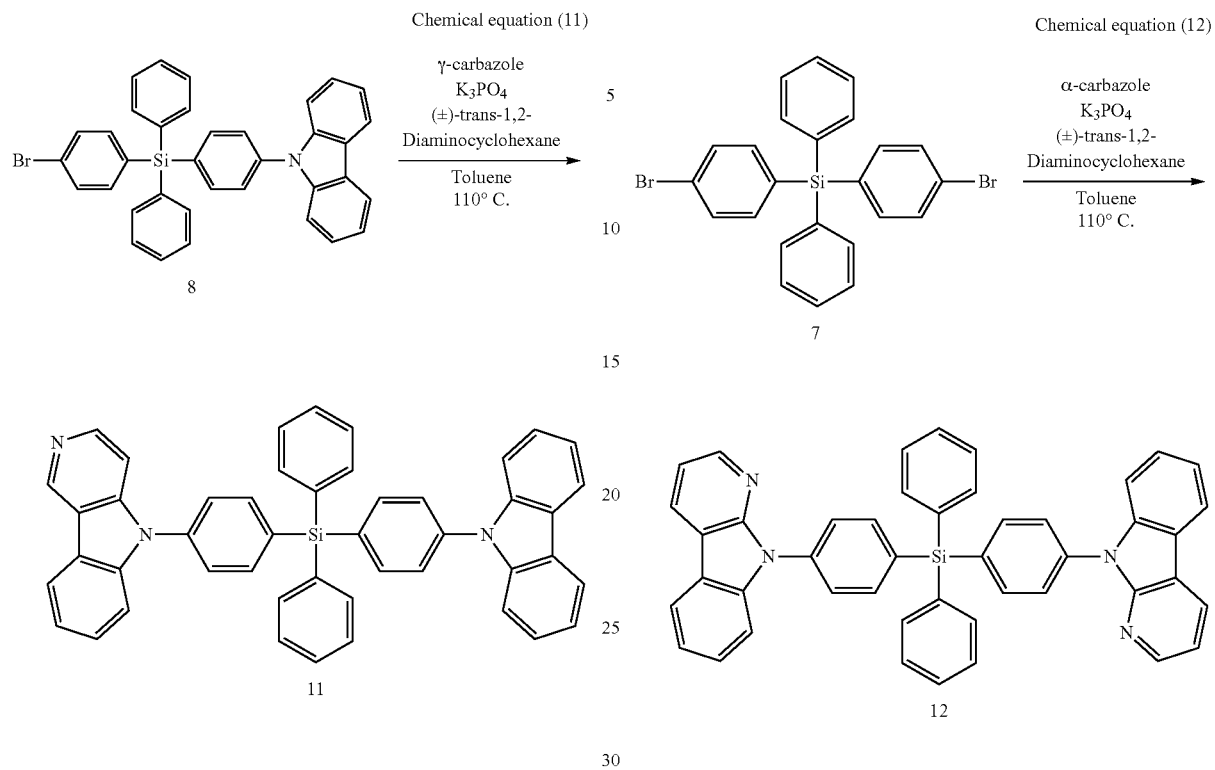

Example 12: Synthesis of Chemical Formula (4) (Di-α-CbSi)

Compound 7 (2.19 g, 4.4 mmol), compound 2 (1.50 g, 8.9 mmol), K₃PO₄ (4.15 g, 19.5 mmol), CuI (169 mg, 0.88 mmol) and a stir bar were placed in a 50 mL single neck bottle. 1,4-Dioxane (22 mL) and (+)-trans-1,2-diaminocyclohexane (0.05 mL, 0.4 mmol) were injected in the single neck bottle, and a condenser was installed. After reacted at 120° C. for 36 hours, the temperature was returned to room temperature. 1,4-Dioxane was removed in a rotary evaporator, and the mixture was filtered through celite. The filtrate was purified by column chromatography using a mixture of dichloromethane and n-hexane (1:1) as eluent. Followed by sublimed, the compound of Chemical Formula (4), Di-α-CbSi (9-(4-((4-(9H-pyrido[2,3-b]indol-9-yl)phenyl)diphenylsilyl)phenyl)-9H-pyrido[2,3-b]indole, 2.07 g, yield: 70%) was obtained. Spectral data as follow: $^1$H NMR (400 MHz, CD$_2$Cl$_2$) δ8.46-8.41 (m, 4H), 8.16 (d, J=7.7 Hz, 4H), 7.92-7.90 (m, 4H), 7.78-7.75 (m, 8H), 7.63 (d, J=8.5 Hz, 2H), 7.53-7.47 (m, 8H), 7.35 (t, J=7.5 Hz, 2H), 7.27 (dd, J=7.7, 4.7 Hz, 2H); 13C NMR (100 MHz, CD$_2$Cl$_2$) δ146.69, 140.10, 138.29, 137.84, 136.83, 134.08, 133.59, 130.33, 128.64, 128.51, 127.34, 126.97, 121.41, 121.35, 121.26, 121.14, 116.75, 116.68, 110.86; HRMS (EI) m/z calcd for C$_{46}$H$_{32}$N$_4$Si, 668.2396, obsd. 668.2511. Anal. Calcd for C$_{46}$H$_{32}$N$_4$Si: C, 82.60; H, 4.82; N, 8.38; Found: C, 82.26; H, 4.86; N, 8.34. The above reaction is represented by the chemical equation (12).

Example 13: Synthesis of Chemical Formula (5) (Di-β-CbSi)

Compound 7 (2.19 g, 4.4 mmol), compound 4 (1.50 g, 8.9 mmol), K$_3$PO$_4$ (4.15 g, 19.5 mmol), CuI (169 mg, 0.88 mmol) and a stir bar were placed in a 50 mL single neck bottle. 1,4-dioxane (22 mL) and (+)-trans-1,2-diaminocyclohexane (0.05 mL, 0.4 mmol) were injected in the single neck bottle, and a condenser was installed. After reacted at 120° C. for 36 hours, the temperature was returned to room temperature. 1,4-dioxane was removed in a rotary evaporator, and the mixture was filtered through celite. The filtrate was purified by column chromatography using a mixture of ethyl acetate and dichloromethane (1:2) as eluent. The compound of Chemical Formula (5), Di-β-CbSi (9-(4-((4-(9H-pyrido[3,4-b]indol-9-yl)phenyl)diphenylsilyl)phenyl)-9H-pyrido[3,4-b]indole, 1.94 g, yield: 65%) as a white solid was obtained. Spectral data as follow: $^1$H NMR (400 MHz, CDCl$_3$) δ8.95 (s, 2H), 8.52 (d, J=5.1 Hz, 2H), 8.20 (d, J=7.7 Hz, 2H), 8.01 (d, J=5.1 Hz, 2H), 7.91 (d, J=8.5 Hz, 4H), 7.72-7.70 (m, 4H), 7.67 (d, J=8.1 Hz, 4H), 7.61-7.54 (m, 4H), 7.53-7.47 (m, 10H), 7.35 (t, J=7.5 Hz, 2H); 13C NMR (100 MHz, CDCl$_3$) δ141.39, 140.24, 138.49, 138.15, 136.81, 136.45, 134.07, 133.34, 133.27, 130.19, 129.22, 128.65, 128.30, 126.11, 121.88, 121.84, 120.86, 114.48, 110.71; HRMS (EI) m/z calcd for C$_{46}$H$_{32}$N$_4$Si, 668.2396, obsd. 669.2470. Anal. Calcd for C$_{46}$H$_{32}$N$_4$Si: C, 82.60; H, 4.82; N, 8.38; Found: C, 82.81; H, 4.79; N, 8.34. The above reaction is represented by the chemical equation (13).

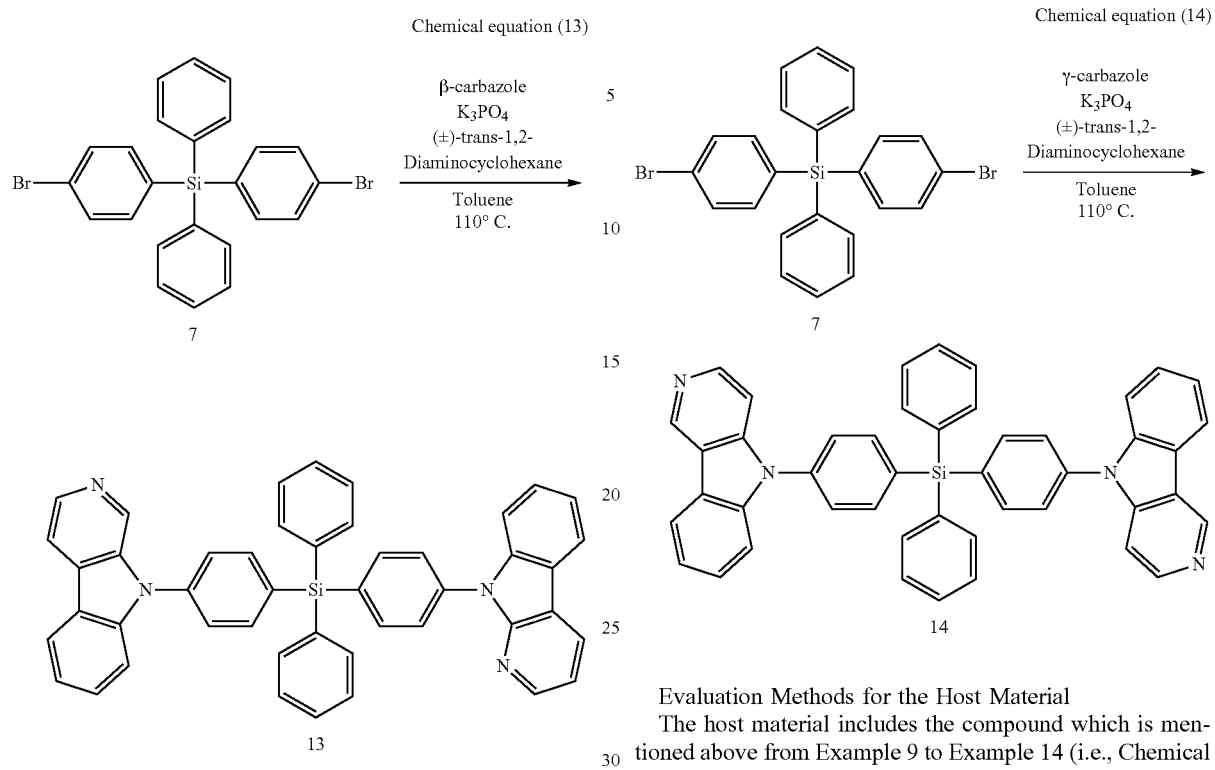

Example 14: Synthesis of Chemical Formula (6) (Di-γ-CbSi)

Compound 7 (2.19 g, 4.4 mmol), compound 6 (1.50 g, 8.9 mmol), $K_3PO_4$ (4.15 g, 19.5 mmol), CuI (169 mg, 0.88 mmol) and a stir bar were placed in a 50 mL single neck bottle. 1,4-dioxane (22 mL) and (+)-trans-1,2-diaminocyclohexane (0.05 mL, 0.4 mmol) were injected in the single neck bottle, and a condenser was installed. After reacted at 120° C. for 36 hours, the temperature was returned to room temperature. 1,4-dioxane was removed in a rotary evaporator, and the mixture was filtered through celite. The filtrate was purified by column chromatography using a mixture of ethyl acetate and dichloromethane (1:1) as eluent. The compound of Chemical Formula (6), Di-γ-CbSi (5-(4-((4-(5H-pyrido[4,3-b]indol-5-yl)phenyl)diphenylsilyl)phenyl)-5H-pyrido[4,3-b]indole, 2.43 g, yield: 82%) as a brown solid was obtained. Spectral data as follow: $^1$H NMR (400 MHz, $CDCl_3$) δ9.47 (s, 2H), 8.62 (d, J=6.0 Hz, 2H), 8.29 (d, J=7.7 Hz, 2H), 7.95 (d, J=8.1 Hz, 4H), 7.70-7.67 (m, 4H), 7.63 (dd, J=7.5, 3.6 Hz, 8H), 7.57-7.48 (m, 10H); $^{13}$C NMR (100 MHz, $CDCl_3$) δ146.21, 141.87, 138.46, 138.24, 136.41, 136.30, 135.98, 132.17, 130.52, 129.29, 128.45, 126.11, 123.56, 121.75, 120.89, 120.69, 117.86, 111.27, 106.28; HRMS (EI) m/z calcd for $C_{46}H_{32}N_4Si$, 668.2396, obsd. 335.1270. Anal. Calcd for $C_{46}H_{32}N_4Si$: C, 82.60; H, 4.82; N, 8.38; Found: C, 82.73; H, 4.81; N, 8.33. The above reaction is represented by the chemical equation (14).

Evaluation Methods for the Host Material

The host material includes the compound which is mentioned above from Example 9 to Example 14 (i.e., Chemical Formula (1) to Chemical Formula (6)). The evaluation methods for the host material is to perform the measurements of the triplet energy level ($E_T$), the glass transition temperature ($T_g$), the pyrolysis temperature ($T_d$), the highest occupied molecular orbital (HOMO), and the lowest unoccupied molecular orbital (LUMO) on the above-mentioned compound of examples, respectively. The triplet energy level measured at low temperature by spectrometer is the basis of selecting the host material of phosphorescent emitter. For blue light-emitting diode, FIrpic ($E_T$=2.65 eV) is a common phosphorescent emitter and the $E_T$ of the host emitter used with FIrpic should be higher than 2.65 eV to avoid low luminous efficiency caused by reverse energy transfer. The glass transition temperature and the pyrolysis temperature respectively measured by differential scanning calorimeter (DSC) and thermogravimetric analyzer (TGA) are considered to be the basis of the stability for the fabrication and performance of unit. HOMO and LUMO are acquired receptively from oxidation potential and reduction potential of the material by using cyclic voltammetry, which can facilitate in searching of an electric charge injection material with small difference energy gap and enhance the efficiency of the unit. The properties of the compounds of Chemical Formula (1) to Chemical Formula (6) are shown in Table 1.

TABLE 1

| Compound | $E_T$ (eV) | $T_g$ (° C.) | $T_d$ (° C.) | HOMO (eV) | LUMO (eV) |
|---|---|---|---|---|---|
| Chemical Formula (1) | 3.02 | 121 | 433 | −5.79 | −2.33 |
| Chemical Formula (2) | 3.10 | 121 | 443 | −5.83 | −2.35 |
| Chemical Formula (3) | 3.08 | 119 | 470 | −5.84 | −2.41 |
| Chemical Formula (4) | 2.98 | 123 | 372 | −5.64 | −2.38 |
| Chemical Formula (5) | 3.07 | 121 | 348 | −5.59 | −2.35 |
| Chemical Formula (6) | 3.11 | 130 | 391 | −5.55 | −2.27 |

According to Table 1, the pyrolysis temperatures of the compound of Chemical Formula (1) to Chemical Formula (6) are all higher than 300° C. It is because that their structures contain multiple benzene rings which are rigid structures, so that the pyrolysis caused by the heat is not easily occurred during the heating process. Based on the reason mentioned above, their derivatives have fine thermal stability and high triplet energy level and are quite beneficial to be the host material in the organic luminescent layer of the organic light emitting diode.

The Efficiency of Compounds (Chemical Formula (1) to Chemical Formula (4)) which were Used as Host Materials in Organic Light Emitting Diodes The unit structure is ITO/TAPC(50 nm)/mCP(10 nm)/host:emitter(30 nm)/DPPS(40 nm)/LiF(0.7 nm)/Al(120 nm). The host materials of the organic luminescent layer are based on the compounds of Chemical Formula (1) to Chemical Formula (4). The host materials were mixed with the guest materials at various ratio of emitter (FIrpic). Herein, the material of first electrode layer of the organic electroluminescent device is ITO. The material of the second electrode layer is aluminum with the thickness of 120 nm. The material of the hole transport layer is TAPC with the thickness of 50 nm. The thickness of the organic luminescent layer is 30 nm. The material of the electron blocking layer is mCP with the thickness of 10 nm. The material of the electron transport layer is DPPS with the thickness of 40 nm. The material of electron injecting layer is LiF with the thickness of 0.7 nm. The above-mentioned layers are made by vapor deposition to form the organic electroluminescent devices of the embodiment, and the driving voltage (V) under the current density of 20 mA/cm$^2$, the maximum current efficiency (cd/A), the maximum power efficiency (lm/W) and the maximum external quantum efficiency (EQE) (%) of the organic electroluminescent devices are measured. The results are shown in Table 2.

TABLE 2

| Unit [a] | driving voltage(V)[b] | maximum current efficiency (cd/A) | power efficiency (lm/W) | EQE (%) |
|---|---|---|---|---|
| Chemical Formula (1) -12% | 7.83 | 55.24@4 V | 50.56@3.0 V | 24.85 |
| Chemical Formula (2) -21% | 7.06 | 48.22@3.5 V | 43.28@3.5 V | 22.32 |
| Chemical Formula (3) -5% | 6.78 | 44.73@3.5 V | 40.15@3.5 V | 18.68 |
| Chemical Formula (4) -21% | 7.71 | 56.08@3.5 V | 50.34@3.5 V | 26.02 |

[a] the doping concentration of FIrpic
[b] the unit of operation voltage under the current density of 20 mA/cm$^2$ The organic electroluminescent devices shown in Table 2 not only have low driving voltages but also have the fine current efficiency, power efficiency and external quantum efficiency. Accordingly, the host materials of the present invention have high transmission rate of electrons and electron holes, and are not necessarily to be operated under high driving voltage. Also, the external quantum efficiencies of the host materials shown in Table 2 are high as well. Consequently, the host materials of the present invention have higher triplet energy level, which is beneficial to reduce reverse energy transfer and to increase the luminous efficiency of organic electroluminescent device.

In summary, in the organic electroluminescent material and the organic electroluminescent device according to the present invention, a series of bipolar compounds are synthesized by utilizing a silicon atom as a spacer to link a hole-transporting carbazole group and an electron-transporting/hole-transporting carboline group. Alternatively, another series of bipolar compounds are synthesized by utilizing a silicon atom as a spacer to link two electron-transporting/hole-transporting carboline groups. The bipolar compounds of the present invention having high triplet energy level and good thermal stability can be organic electroluminescent materials with high luminous efficiency.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An organic electroluminescent material, comprising a structure of the following General Formula (1),

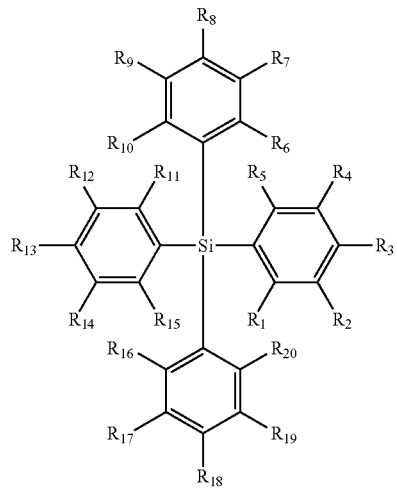

General Formula (1)

wherein R3 is an α-carboline group, β-carboline group or γ-carboline group, R13 is a carbazole group, R1 to R2, R4 to R12 and R14 to R20 are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group, the α-carboline group, β-carboline group or γ-carboline group is attached to General Formula (1) by the nitrogen atom of the five-membered ring of the α-carboline group, β-carboline group or γ-carboline group, and the carbazole group is attached to General Formula (1) by the nitrogen atom of the five-membered ring of the carbazole group.

2. The organic electroluminescent material of claim 1, wherein the alkyl group is selected from the group consisting of a substituted or unsubstituted straight-chain alkyl group and a substituted or unsubstituted branched-chain alkyl group, the cycloalkyl group is a substituted or unsubstituted cycloalkyl group, the alkoxy group is selected from the group consisting of a substituted or unsubstituted straight-chain alkoxy group and a substituted or unsubstituted branched-chain alkoxy group, the haloalkyl group is selected from the group consisting of a substituted or unsubstituted straight-chain haloalkyl group and a substituted or unsubstituted branched-chain haloalkyl group, the thioalkyl group is selected from the group consisting of a substituted or unsubstituted straight-chain thioalkyl group and a substituted or unsubstituted branched-chain thioalkyl group, the silyl group is selected from the group consisting of a substituted or unsubstituted straight-chain silyl group and a substituted or unsubstituted branched-chain silyl group, the alkenyl group is selected from the group consisting of a substituted or unsubstituted straight-chain alkenyl group and a substituted or unsubstituted branched-chain alkenyl group.

3. An organic electroluminescent device, comprising:
a first electrode layer;
a second electrode layer; and
an organic luminescent unit, disposed between the first electrode layer and the second electrode layer, wherein the organic luminescent unit has at least an organic luminescent material as shown in General Formula (1), General Formula (1)

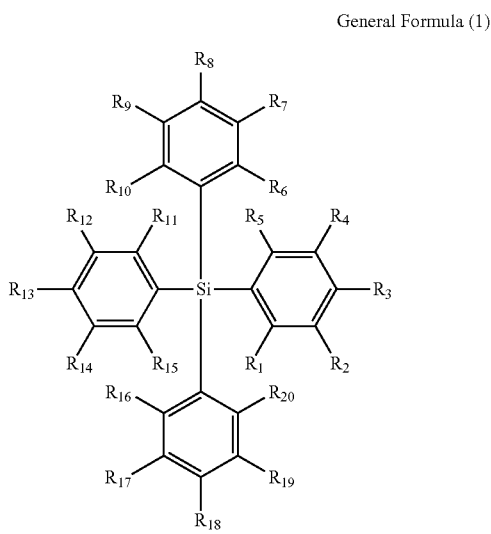

wherein R3 is an α-carboline group, β-carboline group or γ-carboline group, R13 is a carbazole group, R1 to R2, R4 to R12 and R14 to R20 are each independently selected from the group consisting of a hydrogen atom, a fluorine atom, a cyano group, an alkyl group, a cycloalkyl group, an alkoxy group, a haloalkyl group, a thioalkyl group, a silyl group and an alkenyl group, the α-carboline group, β-carboline group or γ-carboline group is attached to General Formula (1) by the nitrogen atom of the five-membered ring of the α-carboline group, β-carboline group or γ-carboline group, and the carbazole group is attached to General Formula (1) by the nitrogen atom of the five-membered ring of the carbazole group.

4. The organic electroluminescent device of claim 3, wherein the alkyl group is selected from the group consisting of a substituted or unsubstituted straight-chain alkyl group and a substituted or unsubstituted branched-chain alkyl group, the cycloalkyl group is a substituted or unsubstituted cycloalkyl group, the alkoxy group is selected from the group consisting of a substituted or unsubstituted straight-chain alkoxy group and a substituted or unsubstituted branched-chain alkoxy group, the haloalkyl group is selected from the group consisting of a substituted or unsubstituted straight-chain haloalkyl group and a substituted or unsubstituted branched-chain haloalkyl group, the thioalkyl group is selected from the group consisting of a substituted or unsubstituted straight-chain thioalkyl group and a substituted or unsubstituted branched-chain thioalkyl group, the silyl group is selected from the group consisting of a substituted or unsubstituted straight-chain silyl group and a substituted or unsubstituted branched-chain silyl group, the alkenyl group is selected from the group consisting of a substituted or unsubstituted straight-chain alkenyl group and a substituted or unsubstituted branched-chain alkenyl group.

5. The organic electroluminescent device of claim 3, wherein the organic luminescent unit comprises an organic luminescent layer.

6. The organic electroluminescent device of claim 5, wherein the organic luminescent unit further comprises a hole transport layer and an electron transport layer, and the organic luminescent layer is disposed between the hole transport layer and the electron transport layer.

7. The organic electroluminescent device of claim 5, wherein the organic luminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

8. The organic electroluminescent device of claim 5, wherein the organic luminescent layer comprises a host material and a guest material, and the host material is the organic electroluminescent material and the guest material is a phosphorescent material.

9. The organic electroluminescent device of claim 8, wherein the content of the host material in the organic luminescent layer is between 60 vol % to 95 vol %.

10. The organic electroluminescent device of claim 8, wherein the content of the guest material in the organic luminescent layer is between 5 vol % to 40 vol %.

* * * * *